(12) United States Patent
Li et al.

(10) Patent No.: US 9,987,431 B2
(45) Date of Patent: Jun. 5, 2018

(54) TRI-RING SYRINGE

(75) Inventors: Chun Li, Beijing (CN); Yunxing Liu, Beijing (CN)

(73) Assignee: Beijing DBT Medi-Tech Development Co., Ltd., Beijing (CN)

( * ) Notice: Subject to any disclaimer, the term of this patent is extended or adjusted under 35 U.S.C. 154(b) by 0 days. days.

(21) Appl. No.: 14/124,617

(22) PCT Filed: Jun. 6, 2012

(86) PCT No.: PCT/CN2012/076503
§ 371 (c)(1),
(2), (4) Date: May 14, 2014

(87) PCT Pub. No.: WO2012/167720
PCT Pub. Date: Dec. 13, 2012

(65) Prior Publication Data
US 2014/0249411 A1 Sep. 4, 2014

(30) Foreign Application Priority Data

Jun. 8, 2011 (CN) .......................... 2011 1 0151750

(51) Int. Cl.
*A61M 5/31* (2006.01)
*A61M 5/315* (2006.01)
(Continued)

(52) U.S. Cl.
CPC ........... *A61M 5/3134* (2013.01); *A61B 6/481* (2013.01); *A61M 5/007* (2013.01);
(Continued)

(58) Field of Classification Search
CPC .............. A61M 5/3134; A61M 5/3137; A61M 5/31511; A61M 5/3148; A61M 5/3129;
(Continued)

(56) References Cited

U.S. PATENT DOCUMENTS

| 1,798,116 A | * | 3/1931 | Brockway | ...................... 604/220 |
| 4,929,238 A | * | 5/1990 | Baum | ........................... 604/208 |

(Continued)

FOREIGN PATENT DOCUMENTS

| CN | 2686631 Y | 3/2005 |
| CN | 201505350 U | 6/2010 |

(Continued)

OTHER PUBLICATIONS

International Search Report for Application No. PCT/CN2012/076503 dated Sep. 20, 2012.
English Translation of the IPRP and Written Opinion for Application No. PCT/CN2012/076503 dated Dec. 10, 2013.

*Primary Examiner* — Bhisma Mehta
*Assistant Examiner* — James D Ponton
(74) *Attorney, Agent, or Firm* — Jenkins, Wilson, Taylor & Hunt, P.A.

(57) ABSTRACT

A tri-ring syringe which includes a barrel (1) having a distal end and a proximal end. The proximal end of the barrel (1) is provided with a double ring handle. The syringe also includes a plunger (2) including a distal end and a proximal end, the proximal end of the plunger (2) being provided with a single ring handle (5), the distal end of the plunger (2) connecting with a rubber stopper (6) and being inserted into the interior of the barrel (1); and an insertion part (3) connected to the barrel (1) and rotating synchronously with the barrel. The invention allows the torque of the rotation of the barrel (1) to be transmitted outward.

9 Claims, 4 Drawing Sheets

(51) Int. Cl.
*A61B 6/00* (2006.01)
*A61M 5/00* (2006.01)
*A61M 39/22* (2006.01)

(52) U.S. Cl.
CPC ........ *A61M 5/3137* (2013.01); *A61M 5/3148* (2013.01); *A61M 5/31511* (2013.01); *A61M 2005/3139* (2013.01); *A61M 2039/226* (2013.01); *A61M 2205/6045* (2013.01)

(58) Field of Classification Search
CPC ................ A61M 5/3135; A61M 5/315; A61M 2005/3139; A61M 2039/226; A61M 39/20
See application file for complete search history.

(56) References Cited

U.S. PATENT DOCUMENTS

2002/0123737 A1* 9/2002 Hart ...................... A61M 5/007
 604/523
2011/0264037 A1* 10/2011 Foshee ................. A61J 1/2096
 604/88

FOREIGN PATENT DOCUMENTS

| CN | 202105263 U | 1/2012 |
| CN | 102225223 A | 10/2012 |
| GB | 1193179 A | 5/1970 |
| WO | WO 2011/032513 A1 | 3/2011 |

* cited by examiner

TRI-RING SYRINGE

TECHNICAL FIELD

The invention relates to a medical device, and particularly to a tri-ring syringe.

TECHNICAL BACKGROUND

Nowadays, angiography is used to image, diagnose, examine and treat the structure of the cardiovascular. In the process of the angiography, a catheter is inserted into the body of the patient, and a contrast agent is injected into the cardiovascular of the patient to be tested. And then, the region in the patient, having the contrast agent injected, is imaged using an X-ray machine. In the cardiovascular of the patient, as the X-ray passes through the region having the contrast agent, the X-ray is absorbed by the contrast agent. By this way, the image of the contrast agent in the vessel, i.e., the image of the interior of the vessel, is shown on the screen of the X-ray machine and is recorded.

Generally, radiography is an essential technology for examining the angiography of the patient. In addition to a tri-ring syringe, a manifold valve is also required during the process of the angiography. The manifold valve is arranged between a catheter and the tri-ring syringe. Wherein the manifold valve is an essential device for switching among a blood-pressure sensor, a physiological saline supply and a contrast agent supply. In the process of the angiography, the operator is required to use the syringe, at the same time, the operator is also required to set the switches of the manifold valve device frequently. Thus, the known manifold valve is extremely inconvenient for the operator and might affect the security and the efficiency of the operation. Accordingly, there has grown up an urgent need for a new syringe, for obviating the problems as mentioned above.

SUMMARY

For substantially obviating one or more disadvantages of the related art, the present invention provides a tri-ring syringe.

The tri-ring syringe provided in the present invention includes a barrel including a barrel distal end and a barrel proximal end provided with a double-ring handheld part; a plunger including a plunger distal end and a plunger proximal end provided with a single ring handheld part, and wherein the plunger distal end is provided with a rubber plug and the plunger distal end is capable of being inserted into the barrel; an insertion component connected to the barrel and capable of being rotated together with the barrel synchronously.

Wherein the insertion component further comprises: a pedestal; and a plurality of connecting plugs arranged on the pedestal uniformly, and wherein the pedestal is connected to the barrel distal end, and wherein the plurality of connecting plugs are connected to a medical device.

Wherein the pedestal is provided with a groove, and the barrel distal end is provided with a first convex boss, the groove of the pedestal is capable of being connected to the first convex boss of the barrel distal end.

Wherein, the first convex boss has a polylateral shape.

Wherein, the number of the connecting plugs is two.

Wherein, a movable joint is capable of being connected to the barrel distal end.

Wherein, the barrel distal end is provided with a second convex boss, the movable joint has a groove connected to the second convex boss on the barrel distal end.

Wherein, the second convex boss has a circular shape.

Wherein, the medical device is a manifold valve device used for angiography.

Wherein the barrel further comprises graduations corresponding to a volume of fluids received in the barrel, wherein the graduations and the double-ring handheld part are arranged on the same horizontal plane.

Therefore, comparing with the known technologies, by using the tri-ring syringe including a barrel, a plunger and insertion component, the pivoting moment of the barrel can be transmitted to outside when the barrel is rotated.

BRIEF DESCRIPTION OF THE DRAWINGS

The present invention will become more fully understood from the detailed description given herein below for illustration only, and thus are not limitative of the present invention, and wherein.

Figure 1:
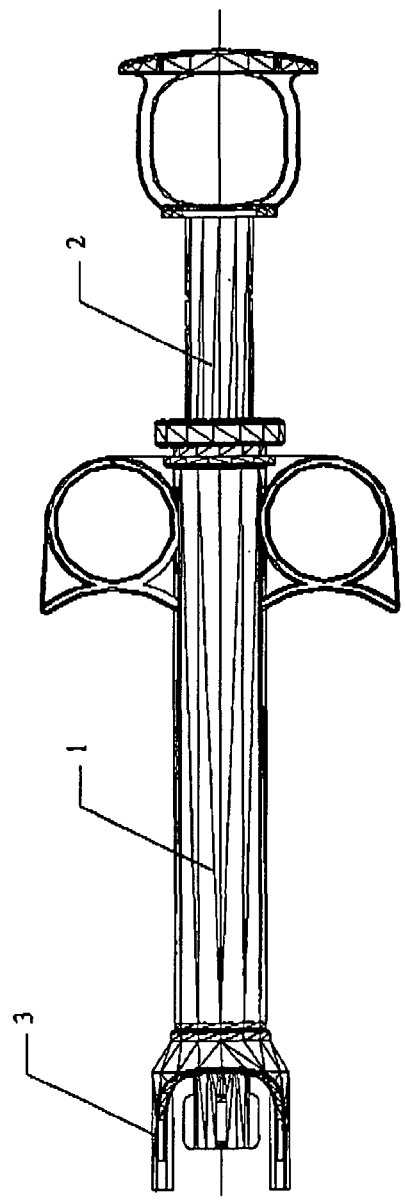
FIG. 1 is a schematic view showing a tri-ring syringe according to one embodiment of the present invention.

SYMBOL DESCRIPTION barrel 1
plunger 2
insertion component 3
pedestal 31
connecting plugs 32
double-ring handheld part 4
single-ring handheld part 5
rubber plug 6
movable joint 7
graduations 8
groove 33
first projecting boss 11
first projecting boss with a polylateral shape 11'
second projecting boss 12
second projecting boss having a circular shape 12'

DETAILED DESCRIPTION

To further clarify the aspects, the opinions and the advantages of the present invention, a more particular description of this invention will be rendered by reference to specific embodiments thereof which are illustrated in the appended drawings.

According to the embodiments of the present invention, the present invention discloses a tri-ring syringe used for angiography.

FIG. 1 is a schematic view showing the tri-ring syringe provided in the present invention. As shown in FIG. 1, the tri-ring syringe includes a barrel 1, a plunger 2 and insertion component 3.

Figure 2:
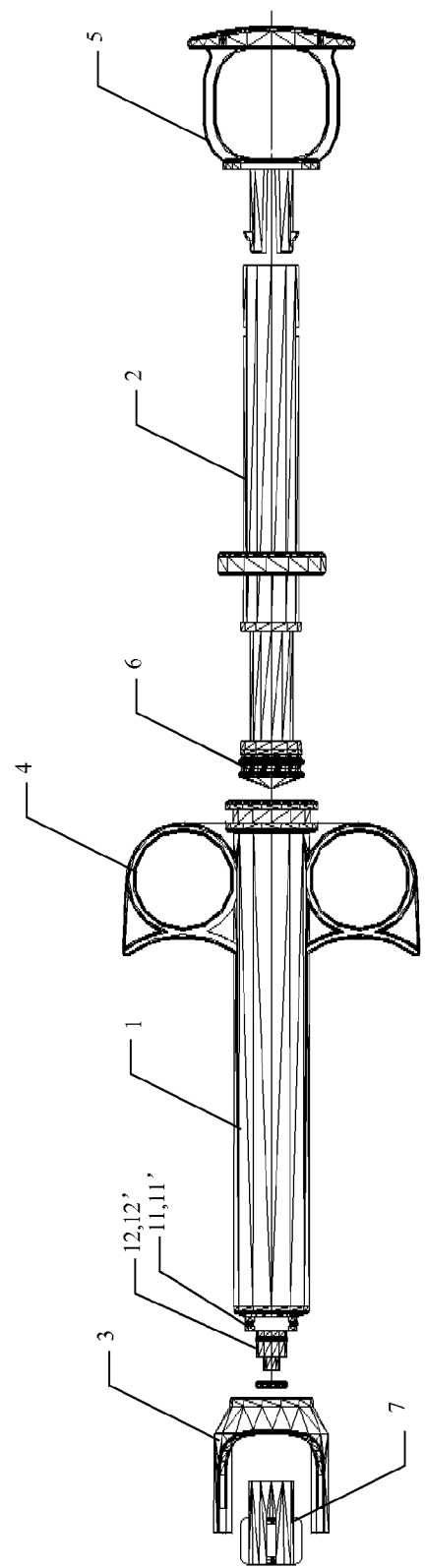
FIG. 2 is an exploded view showing the tri-ring syringe according to the embodiment of the present invention.
Figure 4:
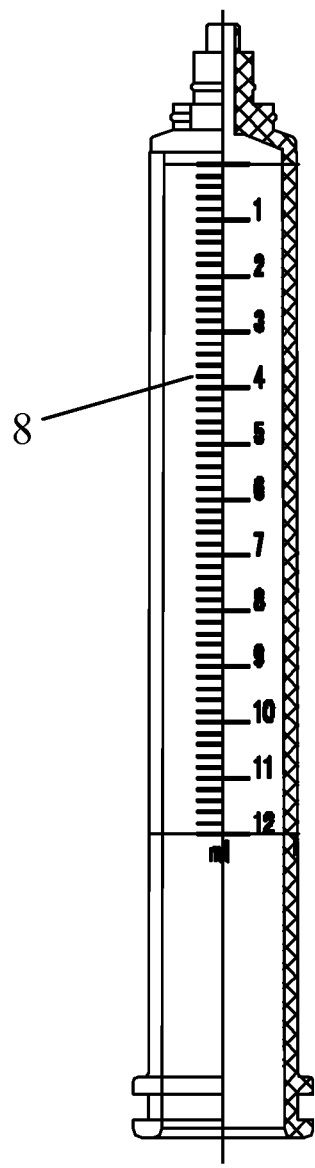
FIG. 4 is a schematic view showing the barrel with graduations according to an embodiment of the present invention.

FIG. 2 is an exploded view of the tri-ring syringe according to an embodiment of the present invention. As shown in FIG. 2, the barrel is configured to have a hollow interior cavity and includes a distal end and a proximal end. The barrel 1 is configured to have a cylinder body, thus a chamber is formed by the inner surface and the distal end of the barrel 1 and is used for receiving medicinal fluids. Here, the proximal end of the barrel has an opening, and the distal end of the barrel 1 has a port used for connecting to a catheter. Furthermore, a double-ring handheld part 4 is provided on the proximal end of the barrel 1 and has a pair of rings arranged on the two sides of the barrel 1 symmetrically. Here, the barrel 1 and the double-ring handheld part 4 can be designed as an integrated structure. Therefore, when conducting the operations of filling and injecting medicinal fluids, the operator can put his/her forefinger and middle finger into the double rings of the double-ring handheld part 4 respectively, for operating the barrel 1. Comparing the syringe without the double-ring handheld part, the structure provided in the present invention is capable of increasing the gripping force exerted on the syringe by the operator. At the same time, as the barrel 1 is used to receive medicinal fluids, some graduations 8 might be marked on the barrel 1 for measuring the volume of the fluids received in the barrel, as shown in FIG. 4.

The plunger 2 includes a distal end and a proximal end. The distal end of the plunger 2 is capable of being inserted into the barrel 1 through the proximal end of the barrel. A single-ring handheld part 5 is provided on the proximal end of the plunger 2. In the operations of filling and injecting medicinal fluids, the operator can put his/her thumb in the single ring of the single-ring handheld part 5. Furthermore, the double-ring handheld part 4 and the single-ring handheld part 5 constitute the tri-ring structure of the syringe. Therefore, a variety of operations for the syringe can be implemented by one hand. Particularly, in some complexity operations (such as the operations of filling and injecting medicinal fluids), another hand can get free for performing other operations, thus this one-hand-operated syringe has great advantages. Accordingly, this tri-ring structure provided in the tri-ring syringe disclosed in this invention can improve the working efficiency significantly. It should be noted that, as shown in FIG. 2, the plunger 2 and the single-ring handheld part 5 are designed as two separated elements. In this case, the single-ring handheld part 5 has a protrusion, and the plunger 2 is provided with a bayonet corresponding to this protrusion. In actual operations, the single-ring handheld part 5 is inserted into the plunger 2, and the protrusion of the single-ring handheld part 5 is capable of being gripped with the bayonet of the plunger 2, then the plunger 2 and the single-ring handheld part 5 are coupled with each other for forming an integrated body, thus the plunger 2 can be operated by the thumb. However, the configurations of the plunger 2 and the single-ring handheld part 5 are not limited to the structure shown in FIG. 2, the plunger 2 and the single ring handheld part 5 can also be designed as an integrated structure, while the repetitious details need not be given here.

The distal end of the plunger 2 is provided with a rubber plug 6 which is capable of being inserted into the inner of the barrel 1 through the proximal end of this barrel. By the peripheral sealing surface of the rubber plug 6, the rubber plug 6 is capable of sliding-contacting with the inner surface of the barrel 1, and thus a removable sealing structure is formed.

Figure 3:
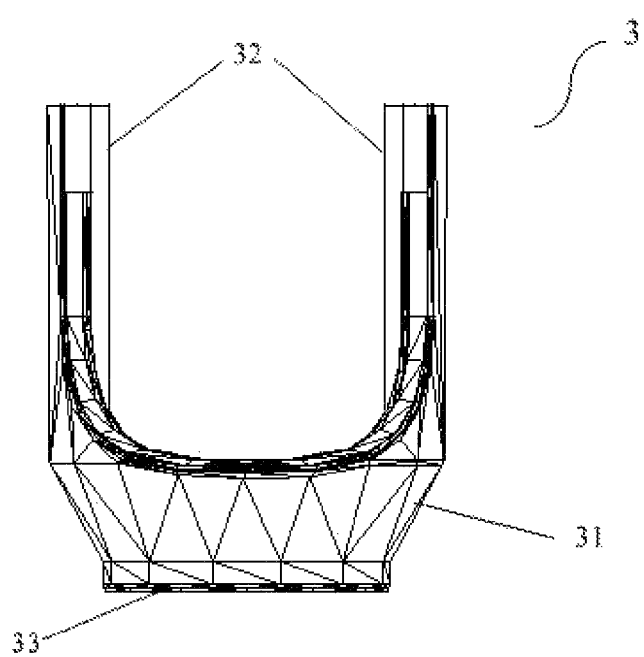
FIG. 3 is a schematic view showing the insertion component according to one embodiment of the present invention.

Please refer to FIGS. 2-3, wherein FIG. 3 is a schematic view showing the insertion component according to an embodiment of the present invention. As shown in the drawings, the tri-ring syringe further includes insertion component 3 connected to the barrel 1. The insertion component is capable of being rotated together with the barrel 1 synchronously and is capable of transmitting the moment of rotation of the barrel 1 out. Specifically, the insertion component 3 includes a pedestal 31 provided with a concave groove 33, wherein the concave groove 33 can be designed to have a polygon shape. Here, a plurality of connecting plugs 32 are arranged on the edge of the pedestal 31 uniformly, wherein the pedestal 31 and the plurality of connecting plugs 32 can be in-mold designed. Furthermore, the distal end of the barrel 1 is provided with a first projecting boss 11 having a shape corresponding to the concave groove 33 of the pedestal 31. Therefore, by connecting the concave groove 33 of the pedestal 31 to the first projecting boss 11 on the distal end of the barrel 1, the insertion component 3 could be fixed to the distal end of the barrel 1.

Furthermore, this insertion component could be referred as "poking fork" and other terms, as long as the insertion component 3 is capable of being rotated together with the barrel 1 synchronously and capable of transmitting the pivoting moment of the barrel 1 outside. Thus, terms used to describe this insertion component cannot be limited by this invention.

Here, a movable joint 7 (a Luer taper connector) is provided on the distal end of the barrel 1, and another end of the moveable joint 7 is capable of being connected to a manifold valve device or being connected to a flexible pipe with an affordable pressure of 250 psi. The movable joint 7 is functioned to provide a connecting joint used for injecting the fluids into the barrel or withdrawing the fluids from the barrel. Furthermore, a second projecting boss 12 can be provided on the distal end of the barrel 1 and configured to have a circular shape 12', wherein the second projecting boss 12 is smaller than first projecting boss 11 and is provided over and located on the first projecting boss 11. The movable joint 7 further has a concave groove corresponding to the second projecting boss 12. Therefore, by connecting the concave groove of the movable joint 7 to the second projecting boss 12 on the distal end of the barrel 1, the movable joint 7 could be fixed to the distal end of the barrel 1.

In practical operations, the pedestal 31 of the insertion component 3 is connected on the first projecting boss 11 of the barrel 1 firstly, and then the movable joint 7 is connected to the second projecting boss 12 of the barrel 1 by applying a O-shape sealing ring, thus the fluids in the barrel 1 could be injected or withdrawn through the movable joint 7, regardless of the effect generated by the insertion component 3. By this way, while the barrel 1 is rotated left and right, the insertion component 3 is capable of being rotated together with the barrel 1 synchronously and is used to transmit the pivoting moment of the barrel 1 outside.

Generally speaking, the tri-ring syringe provided in this invention is used in angiography operation. In this case, the insertion component 3 is connected to a medical device. Preferably, the medical device is a manifold valve device used for angiography. The manifold valve device has sockets corresponding to the plurality of connecting plugs 32 provided on the insertion component 3. By inserting these connecting plugs 32 into the sockets of the manifold valve device, the insertion component 3 is capable of being fixed to the triple three-way valve, thus the tri-ring syringe and the manifold valve device are assembled as an integrated structure. Here, the movable joint 7 is connected to the medicinal fluids input port of the manifold valve device by rotating the movable joint 7, thus the fluids in the barrel 1 could be injected into the manifold valve device or withdrawn from the manifold valve device through the movable joint 7. Therefore, as the barrel 1 is rotated left and right, the insertion component 3 is capable of transmitting the pivoting moment of the barrel 1 to the manifold valve device. Accordingly, as the manifold valve device is required to be rotated, the operator merely needs to operate the barrel 1 for rotating the manifold valve device. And it is not necessary to rotate the manifold valve device directly.

During the processes of connecting or disconnecting of the tri-ring syringe and the manifold valve device, those can be implemented by operating the movable joint 7 provided in the space surrounded by the plurality of connecting plugs of the insertion component 3. Thus, based on the premise that the connecting or the disconnecting between the movable joint 7 and the manifold valve device will not be affected, the number of the plurality of connecting plugs 32 of the insertion component 3 are set according to the actual requirements. Preferably, the number of the plurality of connecting plugs 32 of the insertion component 3 is two. Thus, the movable joint 7 could be plugged or unplugged easily in the space surrounded by the plurality of connecting plugs. However, this invention cannot be limited to this embodiment.

Additionally, in the process of the angiography operation using the tri-ring syringe provided in this invention, the operator might need to control the volume of the fluids injected, thus the graduations could be marked on the barrel and the double-ring handheld part 5 are arranged on the same plane, for convenient observation.

Accordingly, according to the embodiment provided in this invention, by using the tri-ring syringe including a barrel, a plunger and an insertion component, the pivoting moment of the barrel can be transmitted to outside when the barrel is rotated.

The foregoing embodiment is merely exemplary and is not to be construed as limiting the present invention. It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A tri-ring syringe comprising:
    a barrel including a barrel distal end and a barrel proximal end which is provided with a double-ring handheld part;
    a plunger including a plunger distal end and a plunger proximal end which is provided with a single-ring handheld part, wherein the plunger distal end is provided with a rubber plug and the plunger distal end is configured for insertion into the barrel;
    an insertion component connected to the distal end of the barrel, the insertion component being configured to rotate with the barrel, synchronously, as the barrel rotates, wherein the insertion component comprises a plurality of connecting plugs being spaced apart from each other at regular intervals about a pedestal of the insertion component, and wherein the connecting plugs surround a central axis of the syringe;
    a movable joint connected to the distal end of the barrel, wherein the movable joint is disposed on the central axis and is surrounded by the connecting plugs,
    wherein the movable joint is in fluid connection with the barrel,
    wherein the pedestal is connected to the barrel distal end,
    wherein each of the plurality of connecting plugs is configured to connect with a seat of a medical device such that the syringe connects to the medical device via the movable joint and by the connecting plugs,
    wherein the device is configured such that upon connection of the plurality of connecting plugs to the seat of the medical device, a moment of rotation of the barrel is configured to be transmitted to the medical device for the purpose of rotating the medical device, and
    wherein the movable joint can rotate independently from the insertion component and the syringe barrel.

2. The tri-ring syringe according to claim 1, wherein:
    the plurality of connecting plugs is arranged on the pedestal uniformly such that each connecting plug of the plurality of connecting plugs is extending outwardly from the pedestal and away from the distal end of the barrel in a direction that is substantially parallel to a longitudinal axis of the barrel.

3. The tri-ring syringe according to claim 2, wherein the barrel distal end is provided with a first projecting boss.

4. The tri-ring syringe according to claim 3, wherein the first projecting boss has a polylateral shape.

5. The tri-ring syringe according to claim 2, wherein the number of the plurality of connecting plugs is two.

6. The tri-ring syringe according to claim 2, wherein the medical device is a manifold valve device used for angiography.

7. The tri-ring syringe according to claim 1, wherein the barrel distal end is provided with a first projecting boss and a second projecting boss.

8. The tri-ring syringe according to claim 7, wherein the second projecting boss has a circular shape.

9. The tri-ring syringe according to claim 1, wherein the barrel further comprises graduations corresponding to a volume of fluid received therein.

* * * * *